US006201247B1

United States Patent
Lutheran et al.

(10) Patent No.: US 6,201,247 B1
(45) Date of Patent: Mar. 13, 2001

(54) LINE SOURCE FOR GAMMA CAMERA

(75) Inventors: Bruce E. Lutheran, Mentor; Frank P. DiFilippo, University Heights; Daniel Gagnon, Twinsburg, all of OH (US)

(73) Assignee: Picker International, Inc., Cleveland, OH (US)

( * ) Notice: Subject to any disclaimer, the term of this patent is extended or adjusted under 35 U.S.C. 154(b) by 0 days.

(21) Appl. No.: 09/053,938

(22) Filed: Apr. 2, 1998

(51) Int. Cl.[7] .................................................. G01T 1/166

(52) U.S. Cl. ....................................................... 250/363.04

(58) Field of Search .............................. 250/363.04, 362, 250/363.05, 363.03; 378/4

(56) References Cited

U.S. PATENT DOCUMENTS

| 4,755,680 | * | 7/1988 | Logan .............................. 250/363 R |
| 5,099,134 | * | 3/1992 | Hase et al. ......................... 250/505.1 |
| 5,210,421 | | 5/1993 | Gullberg et al. . |
| 5,430,297 | | 7/1995 | Hawman . |
| 5,436,958 | * | 7/1995 | Taylor ................................. 378/149 |

(List continued on next page.)

FOREIGN PATENT DOCUMENTS

| WO 91/00048 | 1/1991 | (WO) . |
| WO 97/43667 | 11/1997 | (WO) . |

OTHER PUBLICATIONS

Smith and Jaszczak, "A Rotating Paralled Hole Collimator for High Resolution Imaging of Medium Energy Radionuclides," 1997 IEEE Nuclear Science Symposium, Conference Record, vol. 2, Nov. 9–15 1997, pp. 1018–1022, XP–002109066, Albuquerque New Mexico.

Ronald J. Jaszczak, Ph.D.; "Noniform Attenuation (NUA™) in Cardiac SPECT: Imaging Effects and Compensation Approaches;" Hitachi Press Release 5; Dec. 1997, 7 pgs.

Beekman and Kamphuis; "Effects of Truncation of Transmission Projections on Cardiac SPECT Images Acquired by a Right–Angle Dual–Camera with Half–Fan–Beam Collimators;" IEEE Transactions on Nuclear Science, vol. 45, No. 3, Jun. 1998, pp. 1174–1178.

David R. Gilland, et al., "Transmission Imaging for Nonuniform Attenuation Correction Using a Three–Headed SPECT Camera;" *Journal Nuclear Med.*, vol. 39, No. 6, Jun. 1998, pp. 1105–1110.

(List continued on next page.)

*Primary Examiner*—Constantine Hannaher
(74) *Attorney, Agent, or Firm*—Timothy B. Gurin; John J. Fry; Eugene E. Clair

(57) ABSTRACT

A transmission radiation source assembly suitable for use in both SPECT and PET imaging includes a line source assembly having a medium energy transmission source. The line source assembly includes a primary collimator rotatably disposed about the medium energy transmission source. The primary collimator includes one or more beam limiting slots for shaping the width of a transmission beam emitted from the line source. An on/off collimator is rotatably disposed about the primary collimator and serves to control the on/off state of the line source. The on/off collimator includes a beam exit slot which, when aligned with one of the beam limiting slots allows the transmission beam to exit the line source. In order to sweep the transmission beam across an opposing detector head, the primary collimator and on/off collimator are synchronously rotated about an axis of rotation of the line source with the on/off collimator in the "on" position. In order to reduce the possibility of over saturating an opposing detector head with radiation from the line source, the rate at which the primary collimator and on/off collimator are rotated is such that the transmission beam spends greater time in regions of the examination region having high attenuation characteristics and shorter time in regions having low attenuation characteristics.

51 Claims, 6 Drawing Sheets

U.S. PATENT DOCUMENTS

| | | | |
|---|---|---|---|
| 5,461,232 | * 10/1995 | McCandless et al. | 250/363.04 |
| 5,479,021 | 12/1995 | Morgan et al. . | |
| 5,552,606 | 9/1996 | Jones et al. . | |
| 5,576,545 | 11/1996 | Stoub et al. . | |
| 5,638,817 | 6/1997 | Morgan et al. | 128/653.1 |
| 5,834,780 | * 11/1998 | Morgan et al. | 250/363.04 |
| 5,929,446 | * 7/1999 | Plummer et al. | 250/363.05 |
| 5,936,247 | * 8/1999 | Lange et al. | 250/363.03 |
| 5,959,300 | * 9/1999 | Hines et al. | 250/363.09 |
| 5,990,482 | * 11/1999 | Bertelsen et al. | 250/363.04 |
| 5,999,588 | * 12/1999 | Shao et al. | 378/4 |
| 6,008,493 | * 12/1999 | Shao et al. | 250/363.04 |

OTHER PUBLICATIONS

Robert A. deKemp and Claude Nahmias; "Attentuation correction in PET using single photon transmission measurment;" Med. Phys. 21 (6), Jun. 1994; pp. 771–778.

Joel S. Karp, et al.; "Singles transmission in volume–imaging PET with a $^{137}$Cs source;" Phys. Med. Biol. 40 (1995), pp. 929–944.

U.S. application No. 08/654,542 filed May 29, 1996 of Morgan, et al.; Scanning Line Source for Gamma Camera.

* cited by examiner

LINE SOURCE FOR GAMMA CAMERA

TECHNICAL FIELD

The present invention relates to the art of diagnostic imaging. It finds particular application in conjunction with single-photon emission computed tomography (SPECT) and with positron emission tomography (PET) and will be described with particular reference thereto. It is to be appreciated, however, that the invention will also find application in other nuclear medicine and transmission radiation diagnostic imagers.

BACKGROUND OF THE INVENTION

In nuclear medicine, radiopharmaceutical are commonly injected into the subject's blood stream for imaging the circulatory system or for imaging specific organs which absorb the injected radiopharmaceutical. Depending on the type of radiopharmaceutical injected, either SPECT or PET imaging is typically used to obtain a final image.

In single photon emission computed tomography imaging, a single photon emitting radiopharmaceutical such as $^{201}$Tl is introduced into a subject or object. A detector is placed closely adjacent to a surface of the subject to monitor radiation characteristic of the radiopharmaceutical's decay. The detector includes a collimator which allows only photons traveling along a relatively limited angle of incidence to reach the detector. An image of the subject is reconstructed utilizing the information obtained by the detected photons. While SPECT imaging may be accomplished using a gamma camera having only one detector, gamma cameras having two or more detectors may also be used.

Positron emission tomography is a branch of nuclear medicine in which a positron-emitting radiopharmaceutical such as $^{18}$F-Fluorodeoxyglucose (FDG) is introduced into the body of a patient. Each emitted positron reacts with an electron in what is known as an annihilation event, thereby generating a pair of 511 keV gamma rays. The gamma rays are emitted in directions approximately 180° apart, i.e. in opposite directions. A pair of detectors registers the position and energy of the respective gamma rays, thereby providing information as to the position of the annihilation event and hence the positron source. Coincidence circuitry is used to determine if a pair of gamma rays is detected substantially simultaneously, e.g., in coincidence. Because the gamma rays travel in opposite directions, the positron annihilation is said to have occurred along a line of coincidence connecting the detected gamma rays. A number of such events are collected and used to reconstruct an image. While an imaging apparatus having at least two detectors is required for PET imaging, additional detectors may also be used.

A drawback to both SPECT and PET imaging technique is that the subject or object being imaged may not be completely homogeneous in terms of radiation attenuation or scatter. For example, a human patient includes many different tissue and bone types which absorb or scatter radiation from the radiopharmaceutical to different degrees. Thus, both SPECT and PET images can be made more accurate if they are corrected for the radiation lost to scattering or attenuation along each path through the human.

Accordingly, it is known to measure the actual attenuation coefficients of body tissues by placing a transmission source of gamma radiation such as a line source on one side of the body and measuring the transmission of the gamma radiation through the body. More specifically, gamma radiation originating from the line source and having passed through the body is detected by one of the gamma camera detectors and used to correct for attenuation and possibly scatter in an image reproduced from the detected gamma rays of the radiopharmaceutical. Unfortunately, existing line sources, and existing gamma camera systems that use them, suffer from certain disadvantages.

For instance, as disclosed in U.S. Pat. No. 5,479,021, which is assigned to Picker International, Inc, a fan beam radiation line source is mounted to a rotating gantry between two detectors and opposite a third. A drawback to this mounting arrangement is that it is not applicable to opposed, two detector head system. Further, such mounting arrangement would not be well suited for systems in which detectors move relative to one another since a detector currently positioned opposite the line source may move from that position.

One technique for utilizing a line source in a system having opposed detectors is to mount the line source at the side of one of the opposed detectors. The line source may then direct a fan beam of radiation to the opposed detector. Such a configuration is shown in one embodiment of U.S. Pat. No. 5,210,421 assigned to Picker International, Inc. A drawback to this approach is that the collimator of the opposed detector must be modified to allow detection of the transmitted radiation from the line source. More particularly, the collimator of the opposed detector would need to be configured to receive the fan beam of radiation. In SPECT imaging, such a collimator configuration typically results in a deleterious effect on the detector's field of view and artifacts from data truncation. Further, such mounting configuration is not well suited for systems in which detector move relative to one another.

In U.S. Pat. No. 5,552,606 assigned to ADAC Laboratories, Inc., there is described yet another technique for utilizing a line source for attenuation correction. In the '606 patent, a line source is shown movably mounted to a rail opposite a detector so as to allow the line source to scan a parallel beam of radiation across the face of the opposing detector. Although the line source configuration of the '606 patent does not require that the opposing detector to have a collimator capable of receiving a fan beam of radiation, the line source assembly does necessitate the use of a complex mechanical arrangement to moveably support the line source and track its linear position. Further, the arrangement of the line source in the '606 patent does not allow for detector heads to be arranged opposite one another and is not suitable for use in systems in which detectors move relative to one another.

Still another technique for utilizing a line source in a system having opposed detectors is described in pending U.S. patent application Ser. No. 08/654,542, filed on May 29, 1996 (U.S. Pat. No. 5,834,780) and assigned to Picker International, Inc. In this application, there is described a scanning line source which is movably affixed to a detector face. By moving the line source across the detector face, a parallel beam of radiation may be directed to the opposing detector in a plane substantially orthogonal to its face. Thus, detector heads may be positioned opposite one another while still allowing parallel beam collimators (as opposed to less desirable fan beam collimators) to be used. While application Ser. No. 08/654,542 provides clear advantages over other existing technologies, it requires the use of a mechanical mounting assemblies to affix the line source to a detector. Also, such a configuration is not well suited for use in systems having detectors which move relative one another.

While line sources are utilized in both SPECT and PET imaging, it will be appreciated that the line sources used in one are not compatible for use in the other. More particularly, line sources used in SPECT typically include a low energy isotope such as Gd-153 (100 keV), Tc-99m (140 keV), or Am-241 (60 keV). By comparison, line sources used in PET typically include a high energy isotope such as Ge-68 (511 keV-coincidence) or Cs-137 (622 keV—singles). If the low energy isotopes used in SPECT were replaced with the high energy isotopes used in PET several difficulties would arise. For one, because the radiopharmaceutical injected into a subject in SPECT is typically of low energy, the introduction of high energy radiation from a line source in such a system would require that a detector be capable of reliably detecting radiation in both the low energy and high energy ranges. Similarly, if a low energy isotope from a SPECT system were placed into a line source of a PET system which normally utilize only high energy radiopharmaceutical, the detector would again need to be able to handle a large range of energies. Unfortunately, many detectors are not able to reliably detect and reproduce images across such a large dynamic range of energies as is necessary to produce high-quality attenuation maps. Further, introduction of a high energy isotope to an otherwise low energy SPECT system would result in a significant increase of contamination in the energy window of the low energy radiopharmaceutical. More particularly, image quality is adversely affected since a significant amount of scatter from the radiation of the high energy isotope falls into the energy range of the low energy radiopharmaceutical thereby making it difficult for the detector to distinguish between radiation received from the subject and radiation received from the line source. Similarly, if a low energy isotope were introduced to a PET system having high energy radiopharmaceutical, scatter from the high energy radiopharmaceutical would significantly reduce the ability to detect radiation from the low energy isotope. Thus, line sources are individually configured for use in either a SPECT or a PET system.

Another drawback to the many prior art line source techniques is that radiation emitted by the line source but not attenuated by the subject reaches the detector without substantial attenuation. This "shine by" radiation results in extraneous detector counts and can cause saturation of the detector, leading to inaccuracies in the image data.

The present invention contemplates a new and improved scanning line source which overcomes the above mentioned shortfalls and others.

SUMMARY

A transmission radiation source assembly includes a line source assembly having a medium energy transmission source. The line source assembly includes a primary collimator rotatably disposed about the medium energy transmission source. The primary collimator includes one or more beam limiting slots for shaping the width of a transmission beam emitted from the line source. An on/off collimator is rotatably disposed about the primary collimator and serves to control the on/off state of the line source. More particularly, the on/off collimator includes a beam exit slot which, when aligned with one of the beam limiting slots allows the transmission beam to exit the line source. In order to sweep the transmission beam across an opposing detector head, the primary collimator and on/off collimator are synchronously rotated about an axis of rotation of the line source with the on/off collimator in the "on" position. To turn the line source off, the beam exit slot of the on/off collimator is rotated so as to not align with the beam limiting slot of the primary collimator. In order to improve the count statistics of the transmission data across an opposing detector head, a rate at which the primary collimator and on/off collimator are rotated is such that the transmission beam spends greater time in regions of the examination region having higher attenuation characteristics (i.e. regions providing a lower count rate) and shorter time in regions having low attenuation characteristics (i.e. regions providing a high count rate).

Because the line source provides a medium energy transmission beam, the type of collimator used in SPECT imaging does not effect the ability of the associated detector head to receive the transmission beam. More particularly, as collimators used in SPECT imaging are typically configured to attenuate low energy gamma rays, the medium energy transmission beam is able to substantially pass through the collimators without excessive attenuation losses. Thus, parallel beam collimators which provide the largest field of view in SPECT imaging may be selected regardless of the positioning and movement of the line source. Further, the line source having a medium energy isotope may also be utilized with PET imaging by reducing contamination to the transmission beam which occurs due to scatter from high energy PET gamma rays. The contamination is reduced by sweeping a narrow transmission beam across the opposing detector so as to have a narrow acquisition window with less overall contamination.

According to one aspect a gamma camera system is provided. The gamma camera system includes a gantry disposed about an examination region, at least one detector head mounted to the gantry, the detector head having a radiation sensitive face facing toward the examination region, and a means for emitting medium energy transmission radiation in a direction which traverse at least a portion of the examination region and which is detectable by the radiation sensitive face.

According to another aspect of the present invention, a gamma camera system is provided. The gamma camera system includes a gantry disposed about an examination region and at least one detector head mounted to the gantry. The detector head includes a radiation sensitive face facing toward the examination region. The gamma camera system further includes a means for sweeping a transmission radiation beam emitted from a stationary transmission source across the radiation sensitive face.

According to yet another aspect of the present invention, a method of diagnostic imaging includes the steps of, detecting radiation emitted by an object in an examination region of a nuclear camera, transmitting a radiation beam through at least a portion of the examination region using a transmission radiation source having a medium energy isotope, detecting the radiation beam, and reconstructing an image representation from the radiation emitted by the object and correcting the image representation in accordance with the transmitted radiation beam.

According to still another aspect of the present invention, a method of diagnostic imaging is provided. The method includes the steps of detecting at a radiation sensitive face of a nuclear camera detector head radiation emitted by an object in an examination region, sweeping a radiation beam emitted from a stationary transmission source across at least a portion of the radiation sensitive face, detecting the radiation beam, and reconstructing an image representation from the radiation emitted by the object and correcting the image representation in accordance with the radiation beam.

According to yet still another aspect of the present invention, a method of imaging utilizing a gamma camera is provided. The gamma camera includes a first detector head and a second detector head disposed about an imaging region so as to detect radiation occurring within the imaging region. The method includes the steps of transmitting a first radiation beam through the imaging region to the first detector head using a first transmission radiation source having a medium energy isotope, transmitting a second radiation beam through the imaging region to the second detector head using a second transmission radiation source having a medium energy isotope, detecting the first and second radiation beams, and reconstructing an image representation from the radiation emitted by the object and correcting the image representation in accordance with the first and second radiation beams.

One advantage of the present invention is that a single line source may be used with both SPECT and PET imaging Another advantage of the present invention is that a radiation beam transmitted from a line source may be swept across a detector head without moving the line source.

Another advantage of the present invention is that a parallel beam detector head collimator may be used in SPECT imaging with a stationary line source assembly.

Yet another advantage of the present invention is that the line source is adaptable to gamma camera systems having detector heads which move relative to one another.

Still another advantage of the present invention is that the line source may be repositioned so as to not interfere with movement of the detector heads.

Yet still another advantage of the present invention is that "shine-by" radiation is reduced by varying the sweep rate of a transmission beam from the line source such that the transmission beam spends more time transmitting through regions in the examination region having high attenuation (and a lower count rate) and less time transmitting through regions in the examination region having low attenuation (and a higher count rate).

Still further advantages of the present invention will become apparent to those of ordinary skill in the art upon reading and understanding the following detailed description of the preferred embodiments.

DETAILED DESCRIPTION

Figure 1:
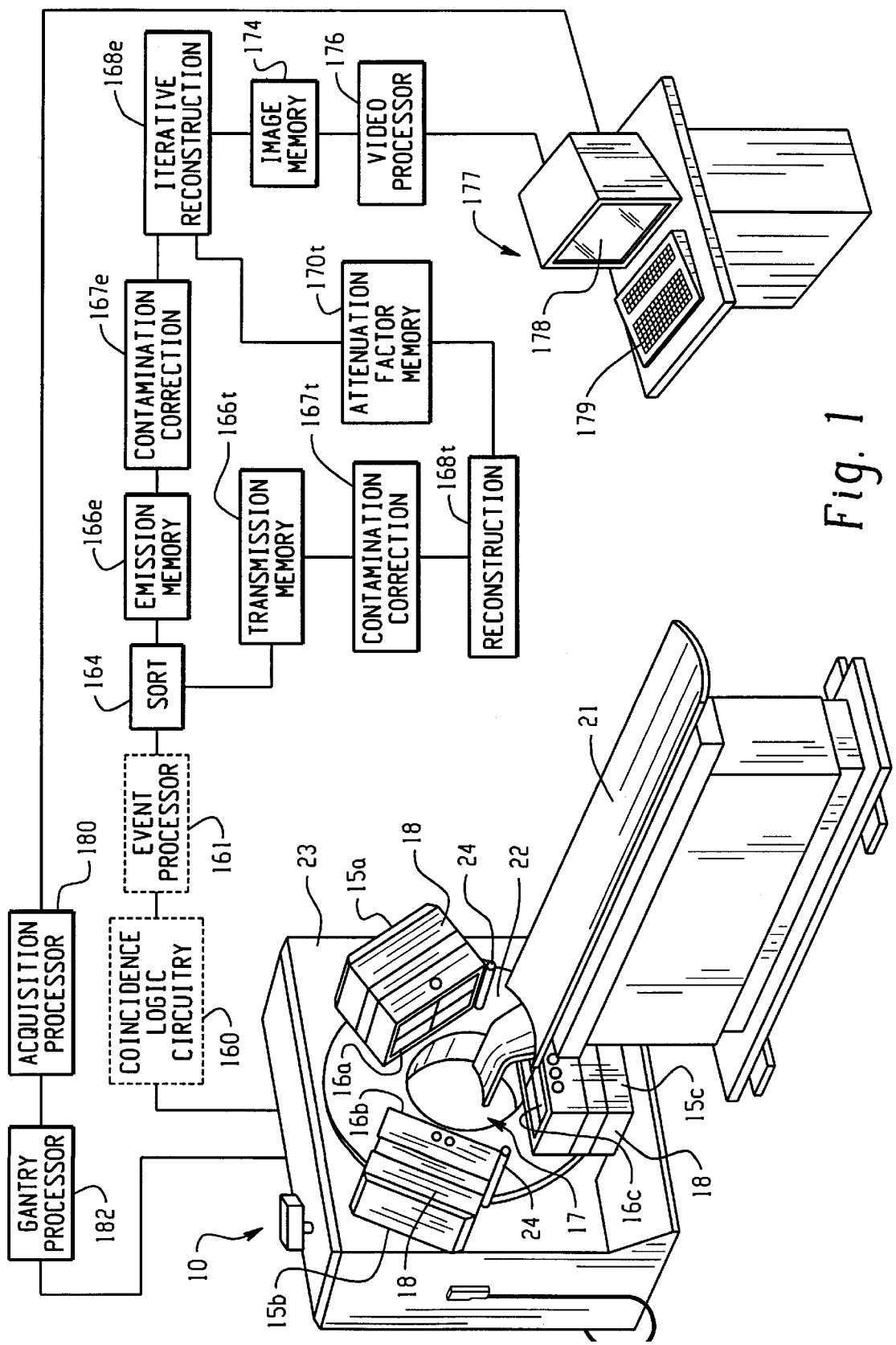
FIG. 1 is a perspective view of a gamma camera system in accordance with the present invention.

The present invention will now be described with reference to the drawings in which like reference numerals are used to refer to like elements throughout.

Turning now to FIG. 1, a gamma camera system 10 is shown having a plurality of radiation detector heads 15a, 15b, 15c (collectively referred to as detector head 15) disposed around a subject examination region 17. The heads 15 are configured to move relative to one another in accordance with known techniques in the art such that, for example, detector head 15a may be positioned opposite detector head 15b or be positioned at any angle ranging from 90–180 degrees with respect to detector head 15b. A patient couch or other subject support 21 selectively supports a region of interest of a subject or object to be examined in the examination region 17.

The detector heads 15 are mounted to a rotatable gantry portion 22 which is connected to a suitable motor and bearing assembly (not shown) supported by a stationary gantry portion 23. The rotatable gantry portion 22 functions as a means for rotating or indexing each detector head around the examination region. Also mounted to the rotating gantry portion 22 are a plurality of mechanical drives (not shown) for moving each of the detector heads 15 independently radially toward and away from the examination region 17 and tangentially to the left and right of the examination region 17. The detector heads 15 are preferably mounted on roller carriages or slide bars for smoother, easier movement.

Each detector head 15 has a collimators 16a, 16b, 16c (collectively referred to as collimators 16) situated in front of a scintillation crystal. The collimators 16 allows only radiation incident the collimators 16 at certain directions to pass to the scintillation crystal for further processing. The collimators 16 are removable attached to the detector head 15 and further serve to define each detector head's 15 overall image resolution and sensitivity. The scintillation crystal responds to incident radiation passing though the collimator 16 by producing a flash of light. An array of photomultiplier tubes which receive the flash of light produce electrical signals in response to each light flash. The relative response of the closest photomultiplier tubes is indicative of a spatial location x, y of a scintillation event produced by a gamma ray being incident on the scintillation crystal. The scintillation crystal, photomultiplier tubes and associated circuitry are situated within a lead casing 18 of each detector head 15. It will be appreciated that any type of gamma ray detector head may also be used.

Figure 2:
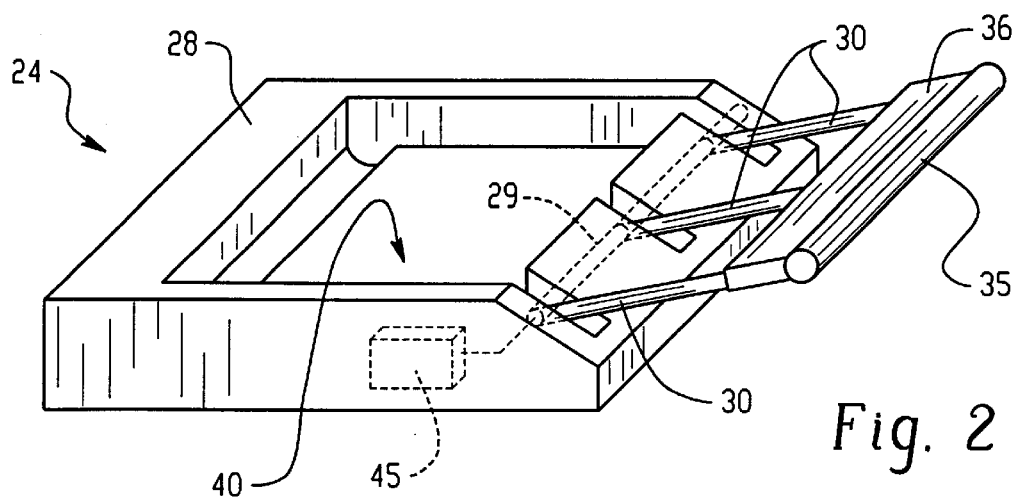
FIG. 2 is a perspective view of one embodiment of a transmission radiation source assembly of the present invention.

As shown in FIGS. 1 and 2, a transmission radiation source assembly 24 is preferably situated to the side of the front face of detector heads 15a and 15b. In the present embodiment the transmission radiation source assembly 24 includes base 28 mounted to the casing 18 of the respective detector head 15 using an adhesive, mounting bolts, and/or other conventional techniques. A retractable arm 30 is pivotably secured to the base 28 via a pivot rod 29. A transmission beam assembly such as line source assembly 35 is secured to an opposite end of the retractable arm 30 through drive box 36. The drive box 36 provides the line source assembly 35 with operating power and control signals. A receiving cavity 40 in the base 28 is sized and shaped to receive the retractable arm 30, drive box 36 and line source assembly 35. A drive control 45 disposed in the base 28 electrically couples to the retractable arm 30 and serves to provide power and control signals to the retractable aim 30 for rotating the retractable arm 30 about the pivot rod 29. The drive box 36 and drive control 45 receive power from the stationary gantry portion 23 and control signals from a gantry processor and acquisition processor as is described in more detail below.

Figure 3:
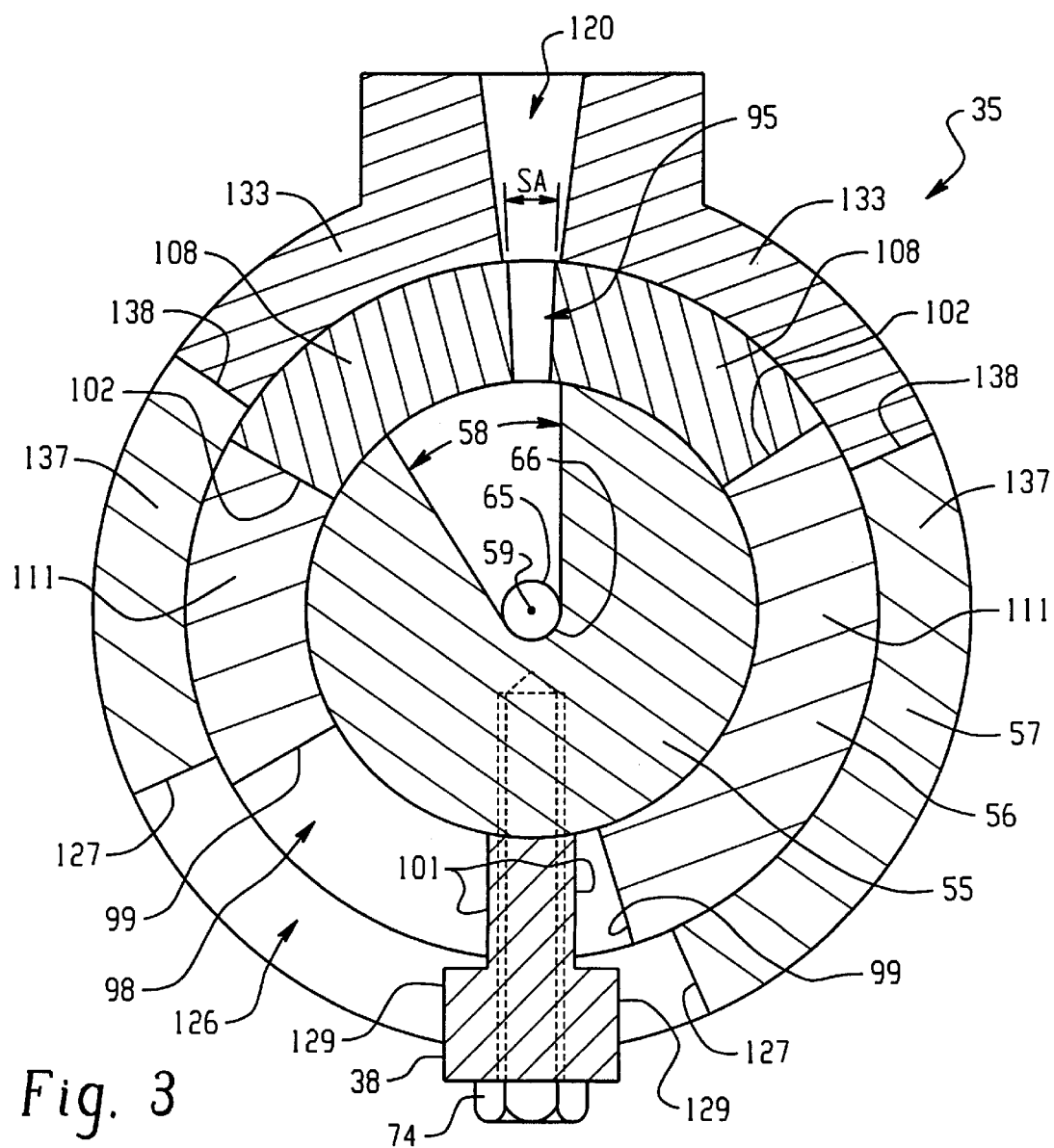
FIG. 3 is an cross-sectional side view of a line source of the of the present invention.

As shown in FIG. 3, the line source assembly 35 includes a cylindrical source holder 55, a primary collimator 56, and an on/off collimator 57. The source holder 55 is comprised of lead or other suitable radiation shielding material. The source holder 55 includes a V-shaped groove 58 defined across its longitudinal axis 59. A line source 65 having a radiation isotope is disposed in a curved radius portion 66 of the V-shaped groove 58 as discussed in more detail below. In the present embodiment, the V-shaped groove 58 provides a maximum 40° fan angle for radiation emitted from the line source 65. It will be appreciated, however, that other suitable fan angles may be selected based on the maximum desired coverage area from the line source assembly 35.

Figure 4:
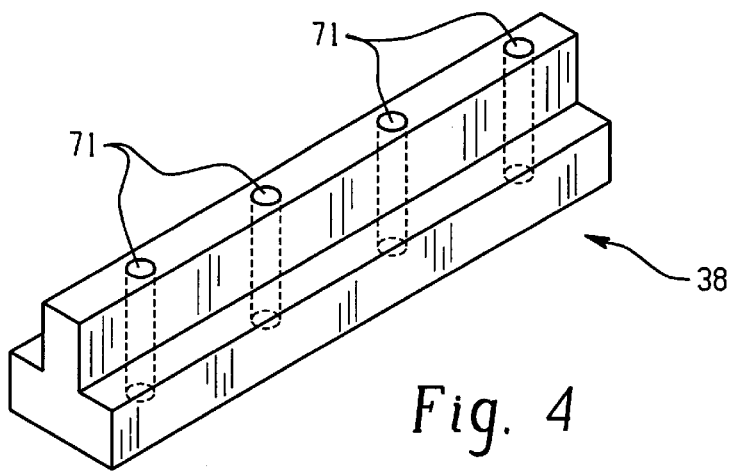
FIG. 4 is a perspective view of a beam support for the line source of the present invention.
Figure 5:
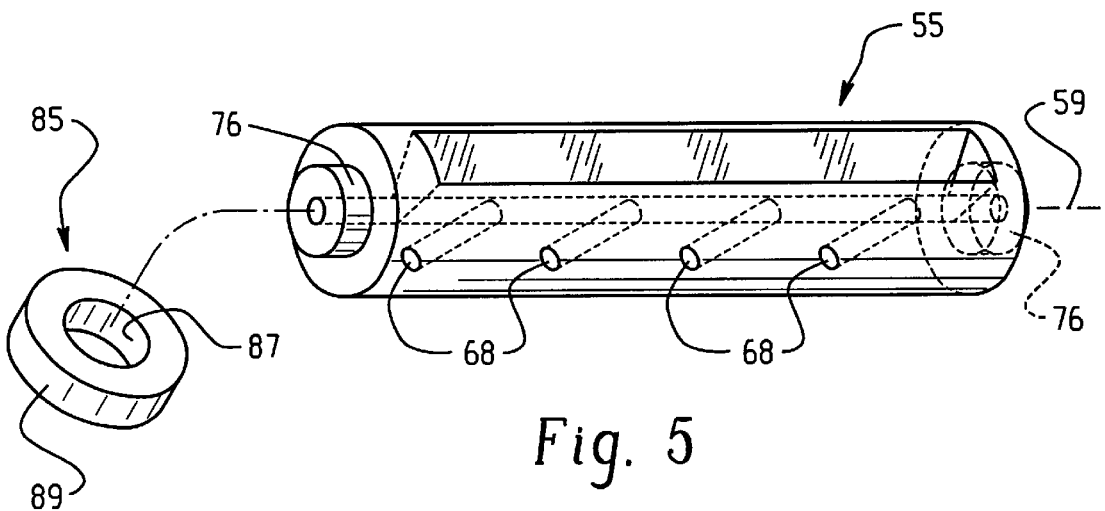
FIG. 5 is a perspective view of a source holder of the line source of the present invention;.

Turning now to FIGS. 4 and 5 the source holder 55, further incudes four threaded apertures 68. The threaded apertures 68 are situated to align with corresponding securing passages 71 defined in a support beam 38. Each threaded aperture 68 and securing passage 71 is sized to receive a corresponding securing bolt 74 (FIG. 3) from within the drive box 36 for rigidly securing the source holder 55 thereto. Although the present embodiment shows four securing bolts 74 used to secure the line source assembly 35, it will be appreciated that other suitable numbers of securing bolts 74 may be used. Further, other conventional mounting and securing techniques could also be used.

As best seen in FIG. 5, a pair of bearing support stems 76 are defined at opposing ends of the source holder 55. A bearing member 85 including a plurality of ball bearings (not shown) is coupled to one of the support stems 76 and provides rotational movement and support to the primary collimator 56 about the axis 59. More particularly, an inner diameter 87 of the bearing member 85 is attached to the bearing stem 76 by way of a frictional press fit, while an outer diameter 89 of the bearing member 85 is sized to press fit within an inner diameter 91 of the primary collimator 56. The plurality of ball bearings disposed in the bearing member 85 allow the outer diameter 89 of the bearing member 85 to rotate relative to the inner diameter 91 thereby allowing for rotational movement of the primary collimator 56 with respect to the source holder 55. A primary collimator gear assembly (not shown) couples to the outer diameter 89 and mechanically rotates the primary collimator 56 in accordance with control signals received from the drive box 36.

Figure 6:
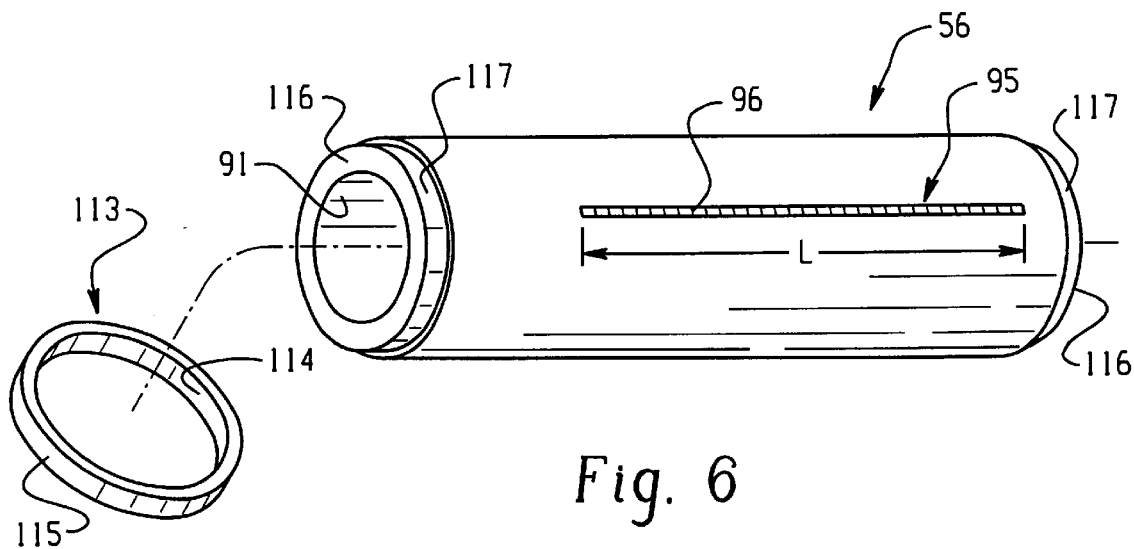
FIG. 6 is a perspective view of a primary collimator of the line source of the present invention.

As shown in FIGS. 3 and 6, the primary collimator 56 includes a beam limiting slot 95. In the present embodiment, the beam limiting slot 95 has a length L and a slot angle SA of 3° with respect to the axis 59 through which radiation from the line source 65 may pass. The size of the slot angle SA defines the width of an acquisition window on the face of the opposing detector head 15 as discussed in more detail below with respect of FIG. 8. The beam limiting slot 95 also includes a one-dimensional collimator 96 disposed therein. The one-dimensional collimator 96 is comprised of a plurality of thin septa mounted within the beam limiting slot 95. The septa are constructed of a material which has good radiation stopping power. Preferably the septa are constructed of tungsten. The one-dimensional collimator 96 ensures that radiation emitted by the line source travels in a direction substantially perpendicular to the axis 59 thereby allowing a detector head to accurately determine an origination point of radiation received from the line source 55. Further, a thin filter may be placed over the septa to reduce low energy emission and/or shape the intensity profile of the transmission beam as is known in the art. While the present embodiment shows the one-dimensional collimator 96 to be disposed in the beam limiting slot 95, it will be appreciated that a one-dimensional collimator may additionally or alternatively be placed in the V-shaped groove 58.

The extent to which the primary collimator 56 may be rotated about the axis 59 is limited by the size of an opening 98 (FIG. 3) in the primary collimator 56. The opening 98 provides a cavity through which the support beam 38 can directly affix to the source holder 55. More particularly, as the primary collimator 56 is rotated clockwise or counter-clockwise such that one of the surfaces 99 of opening 98 comes into contact with a side wall 101 of the support beam 38, the primary collimator 56 is limited from further rotation in that direction.

In the present embodiment, the material of which the primary collimator 56 is comprised varies between two regions having a boundary at 102. Region 108 is defined as the region of the primary collimator 56 which may be exposed to radiation from the line source 65 and therefore is comprised of lead or other radiation blocking material. Region 111, on the other hand, is the region of the primary collimator 56 which will not be exposed to radiation given the limited range of rotational movement of the primary collimator 56. Thus, in order to reduce the overall weight of the primary collimator, region 111 is comprised of aluminum. While the primary collimator 56 of the present embodiment is shown to be made of a combination of lead and aluminum, it will be appreciated that other suitable materials may also be used. Further, although the present embodiment shows the beam limiting slot 95 to have a 3° slot angle, it will be appreciated that various beam slot sizes may be selected. Alternatively, if a fan beam were desired as opposed to a sweeping beam, the slot 95 may be sized to match the size of the fan beam originating from the V-shaped groove 58. Additionally, it is possible to include several slots in the primary collimator 56 each of varying sizes and cach spaced so as to not interfere with one another.

Referring to FIG. 6, the primary collimator 56 includes a pair of outer bearing receiving stems 116 for receiving a pair of outer bearing members 113. Similar to the bearing member 85 described above, the outer bearing member 113 includes an inner diameter 114 and outer diameter 115. The inner diameter 114 is sized to frictionally press fit with an outer surface 117 of the bearing receiving stems 116. The outer diameter 115 is sized to frictionally press fit within an inner surface 118 of the on/off collimator 57 (see FIG. 7). The outer bearing member 113 thereby provides for independent support and rotation of the on/off collimator 57 about the axis 59 with respect to the primary collimator 56. An on/off collimator gear assembly (not shown) couples to the outer diameter 115 and mechanically rotates the on/off collimator 57 in accordance with control signals received from the drive box 36.

Figure 7:
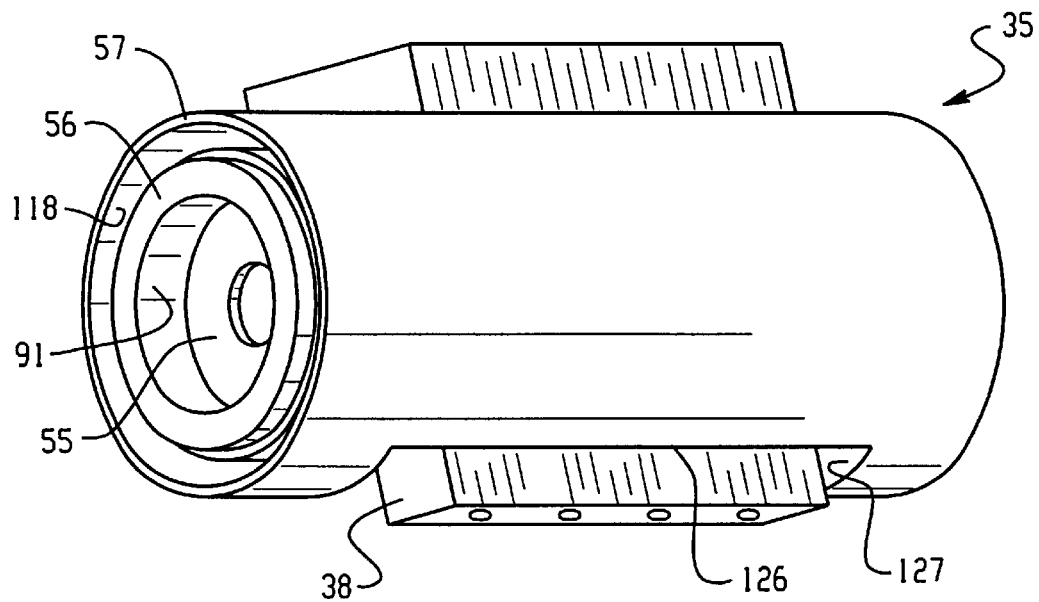
FIG. 7 is a perspective view of the line source of the present invention.

Referring now to FIGS. 3 and 7, the on/off collimator 57 includes a beam exit slot 120. The beam exit slot 120 of the present embodiment is sized to have a 6° slot angle opening. Of course the beam exit slot 120 may be varied in size and under typical circumstances will be slightly wider than the widest beam limiting slot 95 in the primary collimator 56. Similar to the primary collimator 56, a range of rotation of the on/off collimator is limited by opening 126 through which the support beam 38 passes. More particularly, as the on/off collimator 57 is rotated clockwise or counter-clockwise such that a surface 127 of the opening 126 comes into contact with a lower side wall 129 of the support beam 38, the on/off collimator 57 is limited from further rotation in that direction. The material of the on/off collimator 57 is lead in region 133, and aluminum in region 137 divided by boundary 138 for reasons similar to that described above with respect to the material of the primary collimator 56.

According to the present invention the line source 65 (FIG. 3) disposed in the line source assembly 35 consists of a medium energy isotope. As discussed in more detail below, a medium energy isotope allows for line source assembly 35 to be used with both PET and SPECT imaging. In the preferred embodiment the radiation source is the isotope Ba-133 which has a half life of approximately 10.5 years and a principal emission at 356 keV. Other medium energy isotopes having energy levels approximately ranging between 250 keV and 400 keV, such as I-131 (364 keV), may alternatively be used. Further, the present invention also allows for low energy and high energy isotopes such as Tc-99m (140 keV), Tl-201 (70 keV), Cs-137 (662 keV) to be used in the line source assembly 35. However, in such cases some benefits, including the benefit of utilizing the same isotope and line source assembly 35 with both PET and SPECT, are typically diminished.

With reference again to FIG. 1, a reconstruction technique for a gamma camera having both emission and transmission data is provided. Of course, the reconstruction technique changes according to the types of radiation collected and the types of collimators used (i.e., fan, cone, parallel beam). Preferably, however, the detector head collimators of the present embodiment are all of parallel beam type.

Initially, transmission radiation from the line source assembly 35 is typically normalized by a blank scan prior to imaging so as to adjust for any non-uniformities in detecting such radiation across the detector head. Next, emission radiation from the radiopharmaceutical introduced into the subject is received by detector heads 15 and emission projection data is generated. The emission data normally contains inaccuracies caused by varying absorption characteristics of the subject's anatomy. If the radiopharmaceutical introduced into the subject is one which emits positrons for PET imaging, coincidence logic circuitry 160 is utilized to determine whether gamma rays from a positron event are detected substantially simultaneously, i.e. in coincidence. Further, an event processor 161 determines an x, y position and the energy z of a positron event. Thus, coincidence logic circuitry 160 and event processor 161 are shown in phantom to represent a gamma camera conducting PET imaging. In the preferred embodiment, transmission radiation from the line source assembly 35 is transmitted during the same time period as emission radiation is detected by the detector heads 15. Thus, once the x, y coordinate and energy z is established through the coincidence logic circuitry 160 in PET imaging or by detection of the location of incident gamma rays in SPECT imaging, a sorter 164 sorts the emission data and transmission data on the basis of the relative energies and/or the detected positions. The data is stored in corresponding emission data memory 166e and transmission data memory 166t. Contamination correction 167e is applied to the emission data to correct for emission counts attributable to transmission radiation such as my be caused by scatter or varying composition of the transmission radionuclide source. Contamination correction 167t is similarly applied to the transmission data to correct for transmission counts attributable to emission radiation such as my be caused by scatter or varying composition of the emission radionuclide source. A reconstruction processor 168t reconstructs the transmission data into a transmission image representative of a volume of attenuation factors stored which are stored in a memory 170t. Each voxel value stored in the memory 170t is indicative of attenuation of tissue in a corresponding location within the patient. A reconstruction algorithm 168e reconstructs the emission data and also corrects the reconstructed image based on the attenuation factors contained in the attenuation correction factor memory 170t. The reconstructed image representation is stored in a volumetric image memory 174. A video processor 176 withdraws selected portions of the data from the image memory 174 to generate corresponding human-readable displays on a video monitor 178. Typical displays include reprojections, selected slices or planes, surface renderings, and the like.

An operator interface 177 includes the video monitor 178 and a keyboard 179. The operator interface 177 couples to the gamma camera system 10 through acquisition processor 180 which controls the transmission source assembly 24 and gantry processor 182 which controls detector head 15 positioning and rotational speed. The keyboard 179 enables the operator to control the image reconstruction process, the selection of displayed data, the selection of preselected scanning procedures, movement of the detector heads 15 radially toward and away from the examination region 17 and circumferentially with respect to one another, positioning the patient couch 21, the position of the line source assembly 35, the sweep rate of the radiation beam emitted from the line source assembly 35, and other custom operations as discussed in more detail below.

Figure 8:
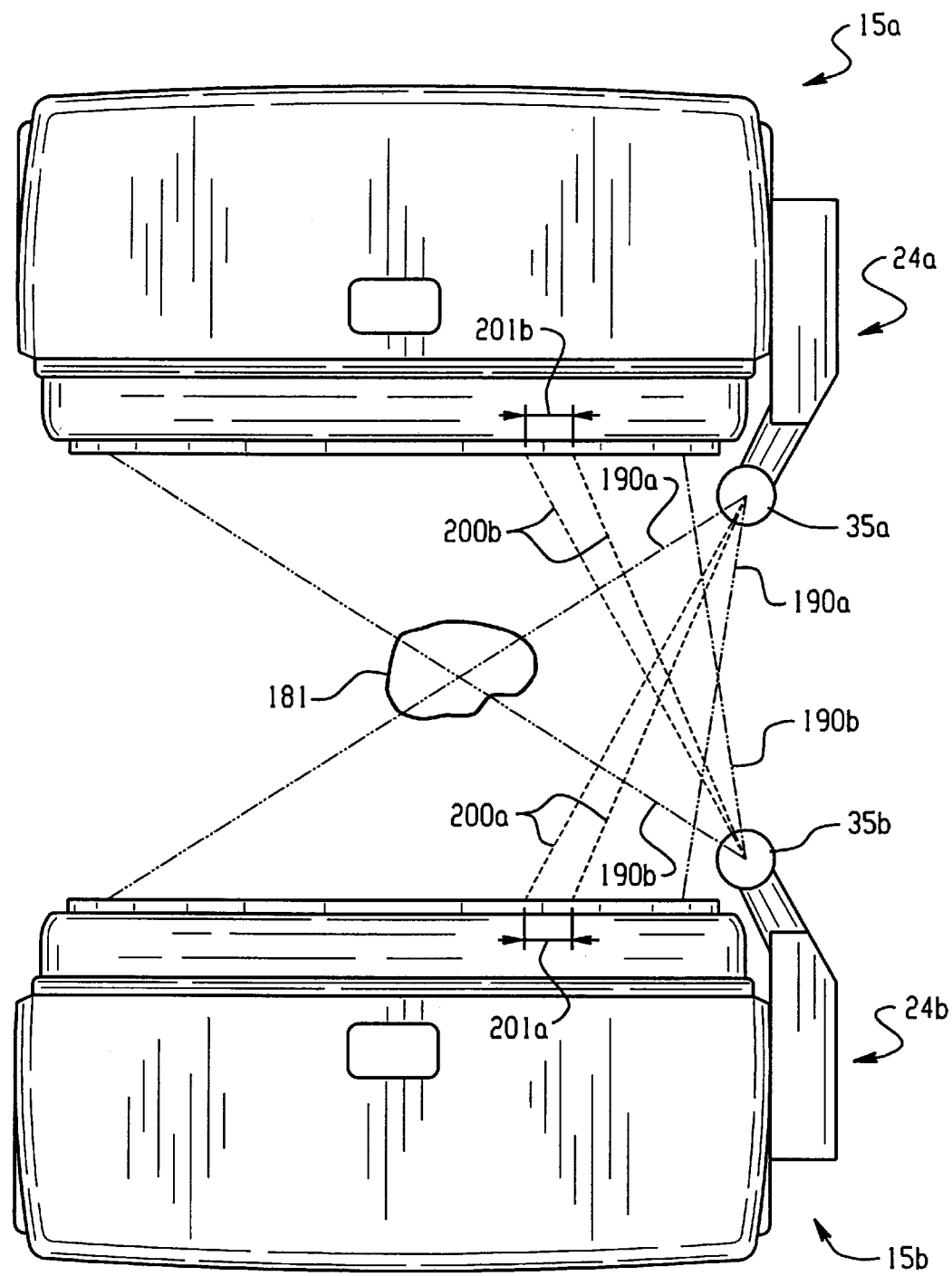
FIG. 8 depicts one embodiment of the present invention in which transmission radiation source assemblies are coupled to opposing detector heads.
Figure 9:
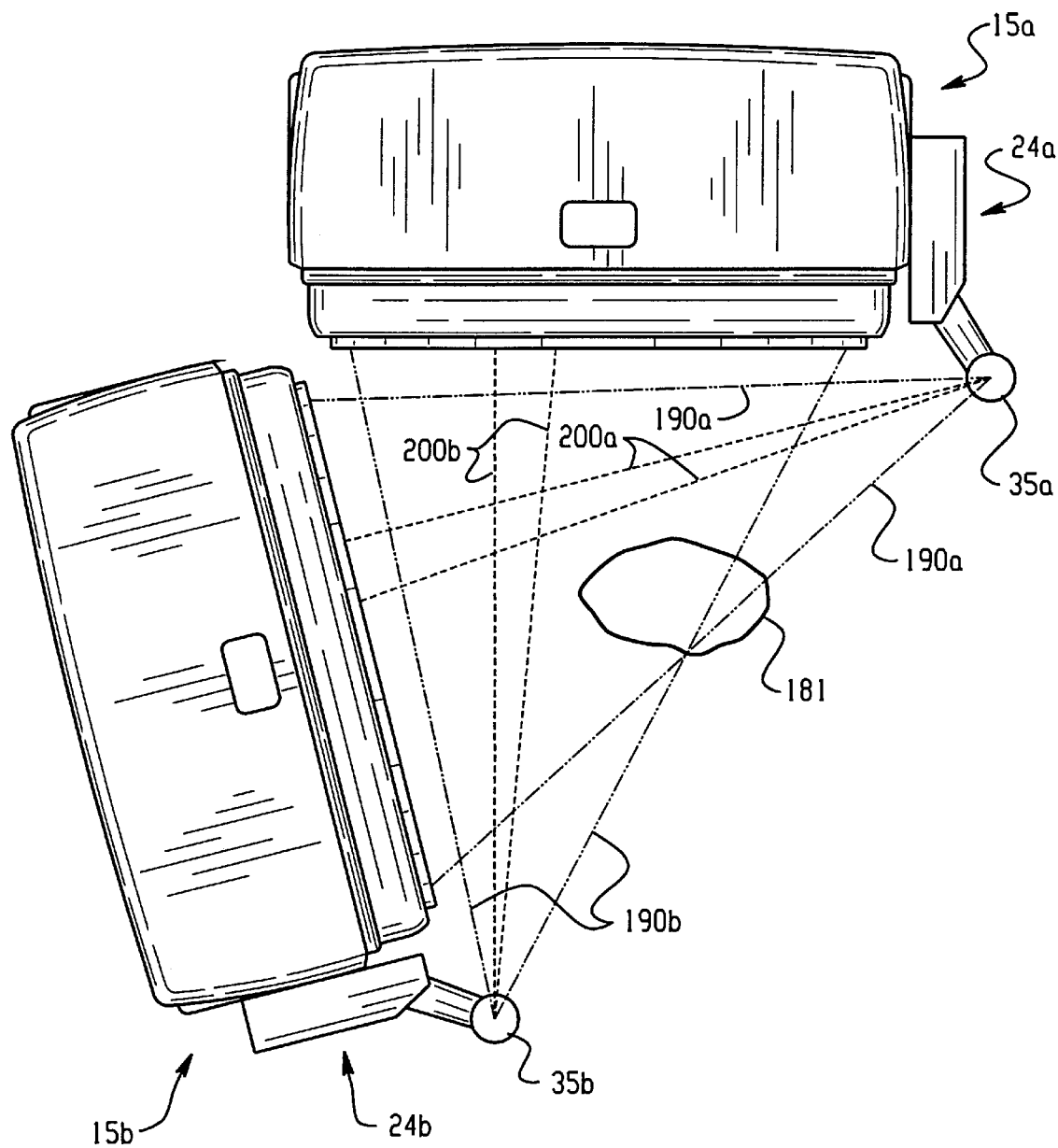
FIG. 9 depicts another embodiment of the present invention in the detector heads having the transmission radiation source assemblies of FIG. 8 are rotated relative to one another about the examination region.

Referring now to FIGS. 8 and 9, the operation of the present invention is discussed in more detail. For exemplary purposes, only two detector heads 15 are shown in FIGS. 8 and 9, however, it will be appreciated that a gamma camera system having only one detector head or three or more detector heads fall within the scope of the present invention. As shown in FIG. 8, two detector heads 15a, 15b, of the gamma camera system 10 are positioned opposite one another for imaging a subject 181. Each detector head 15a, 15b is shown to have a corresponding transmission source assembly 24a, 24b mounted thereon. A field of view of a line source assembly 35a corresponding to transmission source assembly 24a is shown to have an outer perimeters 190a. Similarly, a field of view of a line source assembly 35b corresponding to transmission source assembly 24b is shown to have an outer perimeter 190b. The field of view of the lines sources 35a, 35b are defined by the angle of their corresponding V-shaped grooves 58 as discussed above. In the preferred embodiment, a narrow beam of transmission radiation 200a, 200b, the width of which is defined by the beam limiting slot 95 of the line source assembly 35, is scanned between the outer perimeters 190a, 190b at a specified rate in order to obtain attenuation correction information.

More particularly, upon injecting the subject 181 with a radiopharmaceutical and initiating an imaging procedure, an operator through operator interface 177 instructs the acquisition processor 180 to sweep a transmission beam 200a, 200b from each line source assembly 35a, 35b across the face of the opposing detector head 15a, 15b. In the present embodiment, each line source assembly 35a, 35b is set to transmit transmission radiation during the same time period in which emission radiation is emitting from the subject. As such, each detector head 15a, 15b, is configured to simultaneously receive emission radiation from the subject and the transmission radiation from transmission beams 200a, 200b. It will be appreciated, however, that the detector heads 15a, 15b may be configured to receive the transmission beams 200a, 200b and emission radiation in sequential time interval, in interleaved time intervals, or otherwise. For instance, if a gamma camera system is not able to simultaneously process coincidence events (emitted from a subject) and singles events (transmitted by the line source) it would be possible to set the gamma camera to process coincidence events at time T1 and singles events at time T2, wherein T1 and T2 occur sequentially in time.

As the transmission beams 200a, 200b are swept across the face or respective detector heads 15a, 15b, the acquisition processor 180 indicates to the sorting circuity 164 (through gantry 23) information as to the location of each detector head's 15a, 15b respective acquisition window 201a, 201b. The acquisition windows 201a, 201b corresponds to the location on the face of each detector head 15a, 15b which is currently irradiated with radiation from the line source assembly 35a, 35b. The acquisition processor 180 (FIG. 1) calculates the location of the acquisition window on the face of a given detector head based the following factors: 1) a known geometrical relationship between the location of the line source and opposing detector head, 2) the beam limiting slot angle 95 of the line source, and 3) the beam sweep rate of the line source. Alternatively, the location of the acquisition window for a variety of known detector head positioning and line source settings may be pre-stored in the acquisition processor 180. As will now be discussed, the moving acquisition window is useful to allow a line source 65 having a medium energy isotope to be used in both SPECT and PET imaging.

In SPECT imaging, the emission radiation from the radiopharmaceutical is of low energy and according to the present embodiment the transmission radiation from the line source assembly 35 is of medium energy. As such, scatter from the medium energy transmission radiation which falls into the low energy range may be detected thereby contaminating the low energy emission data and degrading image quality. By tracking the acquisition window of each line source assembly 35, however, the sorting circuitry 164 is directed to only consider emission data received outside of the moving acquisition window at any give time when producing a final image of the subject. As the data received outside the acquisition window contains little to no scattered radiation from the line source assembly 35, such data accurately represents the subject being imaged. With respect to radiation received within the acquisition window, the sorting circuitry 164 distinguishes between transmission data and emission data based on the energy of the detected gamma rays. A complete set of emission and transmission data is thereby obtained by virtue of accumulating emission radiation outside the acquisition window and transmission radiation inside the acquisition window as a transmission beam from the line source is swept across the face of the detector head.

With respect to PET imaging, the radiopharmaceutical introduced into a subject generates radiation having higher energy than the medium energy transmission radiation from the line source assembly 35. As such, scatter from the radiopharmaceutical's emission data may contaminate the collection of transmission data within the acquisition window. However, the amount of scatter from the emission data which contaminates the transmission data is proportional to the width of the acquisition window which is in turn defined by the size of the beam limiting slot 95. More particularly, as the width of the beam limiting slot 95 increases, so does the amount of contamination to the transmission data. Thus, by utilizing a narrow beam limiting slot 95, the acquisition window at any given time is narrowly defined so as to minimize the amount of contamination to the transmission data in PET imaging thereby allowing a medium energy isotope to be used in the line source assembly 35.

Referring to FIG. 3, in order to sweep a transmission beam across a detector head, the present invention selectively rotates the primary collimator 56 and on/off collimator 57 of the line source assembly 35 about axis 59. Positioning of the primary collimator 56 and on/off collimator 57 is controlled by acquisition processor 180 (FIG. 1) through the drive box 36 (FIG. 2). More particularly, prior to activation of the line source assembly 35, the on/off collimator 57 is positioned such that region 133 of the on/off collimator 57 completely covers the beam limiting slot 95. Further, the primary collimator 56 is positioned such that the beam limiting slot 95 is not aligned with any portion of the V-shaped groove 58. Upon activation of the line source assembly 35, the on/off collimator 57 is positioned such that the beam exit slot 120 is coincident with (i.e. aligned with) the beam limiting slot 95 of the primary collimator 56. Once aligned, both the on/off collimator 57 and the primary collimator 56 are simultaneously and synchronously rotated about the axis 59 at a specified rate so as to maintain the alignment during rotation. As the beam exit slot 120 and beam limiting slot 95 pass across the V-shaped groove 95, a transmission radiation beam 200a, 200b (FIG. 8) is effectively swept across an opposing detector head. Once the beam limiting slot 95 is circumferentially rotated beyond the V-shaped groove 95, rotation of the primary collimator 56 is halted while rotation of the on/off collimator 120 continues until the beam exit slot 120 is no longer aligned with the beam limiting slot 95. It will be appreciated that if at any time during this procedure a signal is sent to the line source assembly 35 to discontinue emission of the transmission beam from the line source assembly 35, the on/off collimator 57 is immediately rotated in a direction opposite the rotational direction of the primary collimator 56 until the beam exit slot 120 is no linger aligned with the beam limiting slot 95.

The sweep rate of the transmission beam from the line source assembly 35 is set so that a full sweep occurs across the detector head 15 in substantially the same amount of time it takes the gamma camera system 10 to receive a complete set of emission data from the subject. For instance, if the imaging time for a given acquisition step is 30 seconds, the sweep rate of each line source assembly 35 is set so that a full sweep occurs in 30 seconds. Although the full sweep occurs in 30 seconds, it will be appreciated that the present invention provides for the sweep rate at any instant in time to be varied to a desired rate. It may be desirous to vary the sweep rate to account for regions of varying attenuation characteristics through which the transmission beam passes. More particularly, as shown in FIG. 8, depending on the positioning and size of the subject 181, the transmission beam 200a from line source assembly 35a may at times pass unattenuated to detector head 15b. In order balance the count statistics in the transmission data, it is preferable to sweep the transmission beam 200a at a faster rate across regions of low or no attenuation. Further, by sweeping the transmission beam 200a at a faster rate across the regions of low attenuation, the line source assembly 35a is able to spend more time directing transmission radiation through the subject thereby obtaining more accurate transmission data. Thus, if a subject being imaged covers an entire region through which a transmission beam from a line source travels, the sweep rate is preferably set to uniformly move across the entire region.

For example, in a line source assembly 35 having a V-shaped groove 58 of 40°, a uniform sweep rate provides for the transmission beam to move at a rate of 1.3 degrees/second. If, however, the subject only covers a middle 50% of the entire region through which the transmission beam from the line source travels, the line source is preferably set to sweep at a rate of 0.8 degrees/second over the regions of no attenuation, and at a rate of 4 degrees/second over the region containing the subject. Alternatively, the on/off collimator of the line source assembly 35a could be set to maintain the line source assembly 35a in an off state during the time in which the transmission beam would otherwise reach the detector head 15b substantially unattenuated from the subject. It will be appreciated that alternative sweep rates may be selected and the present invention is not limited to the sweep rates and sweep times discussed above.

Referring now to FIG. 9, it is shown how the transmission radiation source assemblies 24a, 24b of the present invention may be used in a gamma camera system having detector heads which move relative one another. More particularly, upon the detector heads 15a, 15b moving from the position shown in FIG. 8 to the position shown in FIG. 9, the line sources 35a, 35b are adjusted so that the outer perimeters 190a, 190b of the transmission radiation falls on the face of the detector head to be irradiated. Adjustment of the line source assembly 35 positioning occurs through the acquisition processor 180 which calculates the desired line source positioning based on known geometrical relationships between the line source and the opposing detector head. The acquisition processor 180 then sends a signal to the drive control 45 of the retractable arm 30 (FIG. 2) to reposition the line source assembly 35 accordingly. Thus, as shown in FIG. 9, the retractable arm 30 of each line source assembly 35a, 35b has been repositioned such that the outer perimeters 190a, 190b of the transmission radiation falls directly onto the face of the opposing detector head 15b, 15a, respectively. It will further be appreciated that the line source assembly 35a, 35b of each detector head may be fully retracted into the receiving cavity 40 in the base 28 of the transmission radiation source assembly. Such full retraction of the line source assembly 35a, 35b may, for instance, be desirable when the geometry of two adjacent detector heads are such that a line source assembly 35 extending from a side of the detector head would obstruct the ability of the detector heads to be properly positioned.

It will be appreciated that the line source assembly 35 of the present invention is suitable for use in both SPECT and PET imaging. More particularly, in SPECT imaging, a high or low energy SPECT collimator which is configured to collimate low energy radiation emitted from the subject is placed on each detector head. According to the preferred embodiment of the present invention, a medium energy isotope is utilized by the line source 65. Thus, a substantial portion of the medium energy transmission radiation from the line source 65 is able to pass through the SPECT collimators and reach the detector head. More particularly, for purposes of the present invention, a substantial portion of transmission radiation passing through a SPECT collimator shall mean that at least twenty (10) percent of the transmission radiation incident on a SPECT collimator is able to pass through the SPECT collimator and be detected by the detector head 15. By comparison, if a low energy isotope were used in the line source, then only approximately one (1) percent of the transmission radiation from the line source typically passes through the SPECT collimator. By utilizing a medium energy isotope, the present invention advantageously allows various collimator geometries to be used with SPECT imaging (e.g. parallel beam collimators, fan beam collimators, cone beam collimators, etc.). Since low energy parallel beam collimators typically provide the largest field of view in SPECT for receiving low energy emission data from the subject, such collimator may therefore be selected independent of the placement and movement of the line source assembly 35. Thus, the present embodiment does not require that complex scanning line source assemblies providing parallel beam transmission radiation be utilized in SPECT imaging in order to be able to use a parallel beam collimator. Further, as discussed above, a moving acquisition window is preferably utilized to reduce the effect of contamination to low energy emission radiation resulting from scatter from the medium energy transmission radiation.

With respect to PET imaging, the same line source utilized in SPECT having the medium energy isotope may also be used. More particularly, by utilizing a narrowly defined moving acquisition window (as defined by the beam limiting slot 95), the percentage of the medium energy transmission radiation which is contaminated in minimized so that reliable transmission data may be obtained. As such, the present invention allows the same line source utilized with SPECT imaging to be utilized with PET imaging. Further, as the collimator utilized with PET imaging is typically configured to receive radiation from a variety of angles, the positioning and movement of the line source is not limited to any given configuration.

The invention has been described with reference to the preferred embodiments. Obviously, modifications and alterations will occur to others upon reading and understanding the preceding detailed description. For instance, although the preferred embodiment discusses the line source assembly 35 of the present invention to be coupled to a side of a detector head 15, the line source assembly 35 may alternatively be used in various other known configurations such as with a scanning line source assembly as that described in U.S. Pat. No. 5,479,021, assigned to Picker International, Inc. which is hereby incorporated by reference.

Figure 10:
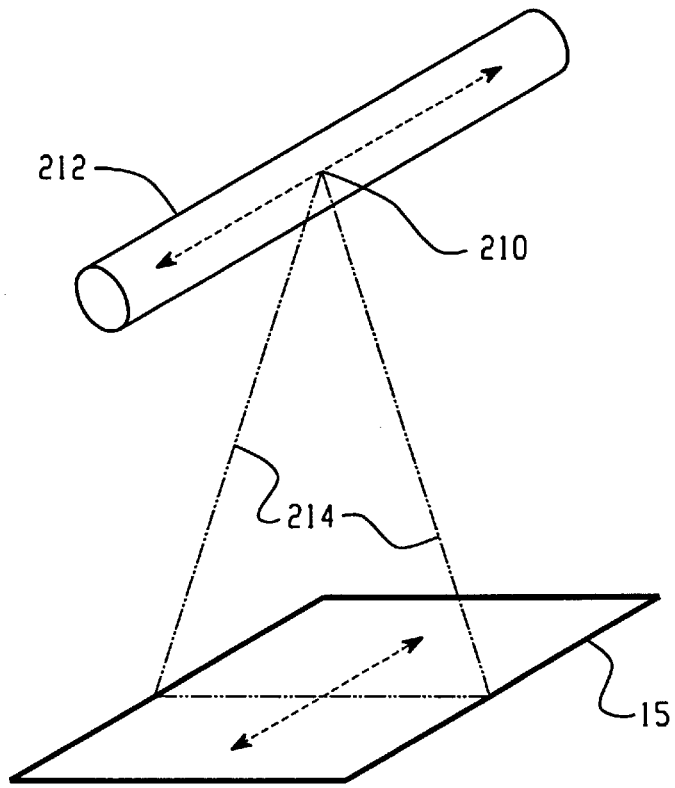
FIG. 10 depicts another embodiment of the present invention in which the transmission source is a scanning point source.

Further, although the preferred embodiment discusses the use of a transmission beam assembly having a line source 65, it will be appreciated that other transmission beam assemblies may alternatively be used. For instance, as shown in FIG. 10, the transmission beam assembly is shown to include a point source 210 disposed in a point source assembly 212. The point source 210 produces a fan beam of radiation 214 which is directed across detector head 15 as the point source 210 is mechanically scanned along a length of the point source assembly 212. Similar to the isotope used in the line source 65, the isotope of the point source 210 is preferably a medium energy isotope thereby providing a medium energy fan beam of radiation 214. It will be appreciated, however, that the point source 210 may alternative include either a high or low energy isotope. Further, it will be appreciated that still other configurations of transmission sources, such as a rectangular bar source, may also be utilized with the present invention to achieve some or all of the benefits described above and others. It is intended that the invention be construed as including all such modifications and alterations insofar as they come within the scope of the appended claims or the equivalents thereof.

What is claimed is:

1. A gamma camera system comprising:

a gantry disposed about an examination region;

at least one detector head mounted to the gantry, the detector head having a radiation sensitive face facing toward the examination region;

a collimator disposed between an object in the examining region and the radiation sensitive face, the collimator having septa; and means for emitting medium energy transmission radiation in a direction which transverses at least a portion of the examination region, at least a portion of the medium energy transmission radiation passing through the septa detectable by the radiation sensitive face.

2. The system of claim 1, wherein the means for emitting medium energy transmission radiation is a transmission radiation source assembly.

3. The system of claim 2, wherein the transmission radiation source assembly includes a transmission beam assembly.

4. The system of claim 3, wherein the transmission beam assembly includes:

a line source having a medium energy isotope; and a primary collimator rotatably disposed about the line source, the primary collimator including at least one beam limiting slot for defining a beam width of the transmission radiation.

5. The system of claim 4, wherein the transmission beam assembly further includes an on/off collimator rotatably disposed about the primary collimator, the on/off collimator including at least one beam exit slot providing a window through which the transmission radiation may pass to the radiation sensitive face.

6. The system of claim 4, wherein the transmission radiation source assembly further includes:

means for adjustably controlling a rotational speed of the primary collimator about the line source.

7. The system of claim 4, wherein the medium energy isotope is one of Ba-133 and I-131.

8. The system of claim 4, wherein the beam limiting slot has a slot angle of substantially between 2 and 5 degrees.

9. The system of claim 2, wherein the transmission radiation source assembly further includes:

a base; and a support arm coupled to the base; and a transmission beam assembly coupled to the support arm.

10. The system of claim 9, wherein the support arm is pivotable in coordination with an angular orientation of the at least one detector head.

11. The system of claim 9, wherein the support arm is pivotably mounted to the base.

12. The system of claim 11, wherein the base includes a receiving cavity for receiving the support arm and the transmission beam assembly.

13. The system of claim 9, wherein the transmission beam assembly includes a medium energy isotope.

14. The system of claim 9, wherein the transmission beam assembly includes one of a line source and a point source.

15. The system of claim 2, wherein the transmission radiation source assembly includes a point source.

16. The system of claim 1, wherein a substantial portion of the medium energy transmission radiation passes through the septa of the collimator.

17. The system of claim 16, wherein the collimator is a parallel beam SPECT collimator.

18. A gamma camera system comprising:

a gantry disposed about an examination region;

at least one detector head mounted to the gantry, the detector head having a radiation sensitive face facing toward the examination region; and means for sweeping a medium energy transmission radiation beam emitted from a stationary transmission source across the radiation sensitive face.

19. The system of claim 18, wherein the means for sweeping includes a primary collimator rotatably disposed about the transmission source, the primary collimator including a beam limiting slot for defining a beam width of the transmission radiation.

20. The system of claim 19, wherein the means for sweeping further includes an on/off collimator rotatably disposed about the primary collimator, the on/off collimator including a beam exit slot for providing a window through which the transmission radiation beam may pass to the radiation sensitive face.

21. The system of claim 19, further including:

means for adjustably controlling a rotational speed of the primary collimator about the transmission source.

22. The system of claim 18, wherein the medium energy transmission radiation ranges in energy from 250 keV to 400 keV.

23. A method of diagnostic imaging comprising the steps of:

collimating emitted radiation from an object in an examining region to a radiation sensitive face of a detector of a nuclear camera, the collimator having septa;

transmitting a radiation beam through at least a portion of the examining region and the septa of the collimator using a transmission radiation source having a medium energy isotope;

detecting the transmitted radiation beam and the emitted radiation;

reconstructing an image representation from the radiation emitted by the object; and correcting the image representation in accordance with the transmitted radiation beam.

24. The method of claim 23, wherein the step of transmitting a radiation beam includes the step of sweeping the radiation beam across the portion of the examination region.

25. The method of claim 24, wherein a rate at which the radiation beam sweeps across the portion of the examination region is substantially constant.

26. The method of claim 24, wherein a rate at which the radiation beam sweeps across the portion of the examination region varies generally inversely to attenuating characteristics of the object.

27. The method of claim 23, wherein the medium energy isotope is one of Ba-133 and I-131.

28. The method of claim 27, wherein the radiation emitted from the object results from one of Tc and Tl.

29. The method of claim 23, wherein the radiation emitted by the object results from a positron annihilation event.

30. The method of claim 23, wherein the radiation emitted by the object is of low energy.

31. A method of diagnostic imaging comprising the steps of:

detecting at a radiation sensitive face of a nuclear camera detector head radiation emitted by an object in an examining region;

sweeping a medium energy radiation beam emitted from a stationary transmission source across at least a portion of the radiation sensitive face;

detecting the transmitted radiation beam;

reconstructing an image representation from the transmitted radiation emitted by the object; and correcting the image representation in accordance with the radiation beam.

32. The method of claim 31, wherein a rate at which the radiation beam sweeps across the radiation sensitive face is substantially constant.

33. The method of claim 31, wherein the step of sweeping a radiation beam includes the step of rotating a primary collimator having a beam limiting slot about the transmission source.

34. The method of claim 31, wherein a rate at which the radiation beam sweeps across the radiation sensitive face is determined by a rotational speed of a primary collimator.

35. The method of claim 31, wherein the transmission source includes a medium energy isotope.

36. A method of imaging utilizing a gamma camera including a first detector head and a second detector head disposed about an imaging region so as to detect radiation emitted by an object within the imaging region, the method comprising the steps of:

collimating the emitted radiation from an object in the imaging region at the first detector head with a first collimator and at the second detector head with a second collimator, the first and second collimator having septa;

transmitting a first radiation beam through the imaging region and through the septa of the first collimator to the first detector head using a first transmission radiation source having a medium energy isotope;

transmitting a second radiation beam through the imaging region and the septa of the second collimator to the second detector head using a second transmission radiation source having a medium energy isotope;

detecting the radiation emitted by the object;

detecting the first and second transmission radiation beams;

reconstructing an image representation from the radiation emitted by the object; and correcting the image representation in accordance with the first and second transmission radiation beams.

37. The method of claim 36, wherein the step of detecting the radiation emitted by the object and the step of detecting the first and second radiation beams occur simultaneously.

38. The method of claim 36, wherein the step of detecting the radiation emitted by the object and the step of detecting the first and second radiation beams occur sequentially.

39. The method of claim 36, wherein the step of detecting the radiation emitted by the object and the step of detecting the first and second radiation beams occur in interleaved intervals.

40. The method of claim 36, wherein the step of transmitting the first radiation beam includes the step of sweeping the first radiation beam across the first detector head.

41. The method of claim 36, wherein the step of transmitting the second radiation beam includes the step of sweeping the second radiation beam across the second detector head.

42. The method of claim 36, further including the step of:

repositioning the first detector head and the second detector head with respect to one another about the imaging region; and repeating the steps of transmitting a first radiation beam, transmitting a second radiation beam, detecting the first and second radiation beams, and reconstructing an image representation.

43. A method of SPECT imaging comprising the steps of:

collimating emission radiation with a collimator having septa, the radiation emitted from an object in an examination region;

detecting at a radiation sensitive face of a nuclear camera detector head, the collimated radiation emitted by the object in the examination region;

transmitting a medium energy transmission beam to the radiation sensitive face, the medium energy transmission beam capable of substantially passing through the septa of the collimator;

reconstructing an image representation from the radiation emitted by the object; and correcting the image representation in accordance with the medium energy transmission beam.

44. The method of claim 43, wherein the collimator is a parallel beam collimator.

45. The method of claim 43, wherein at least ten percent of the transmission beam is capable of passing through the collimator.

46. An imaging apparatus comprising:

a first detector head and a second detector head adapted to detect emission radiation from an object located in an imaging region;

a collimator disposed between a face of the second detector head and the imaging region, the collimator having septa; and a medium energy transmission radiation source mounted alongside the first detector head and adapted to transmit medium energy gamma radiation through at least a portion of the object, the medium energy gamma radiation detectable by the second detector head, wherein at least ten percent (10%) of the medium energy gamma radiation incident on collimator passes through the septa of the collimator.

47. The apparatus of claim 46, wherein the emission radiation is produced from one of Tc and Tl.

48. The apparatus of claim 47, wherein the medium energy gamma radiation is produced from one of Ba-133 and I-131.

49. The apparatus of claim 46, further including coincidence detection circuity.

50. The apparatus of claim 49, wherein the emission radiation is produced from $^{18}$F-Fluorodeoxyglucose.

51. The apparatus of claim 46, wherein an angular positioning of the first detector is adjustable to at least a first and second position, and the position of the transmission source is adjustable so that the transmission radiation emitted by the transmission source transverses through the imaging region at least the first and second position for detection by second detector.

* * * * *